United States Patent [19]

Neef et al.

[11] 4,333,928
[45] Jun. 8, 1982

[54] 16 α-ALKYL STEROIDS, THEIR PREPARATION, AND PHARMACEUTICAL PREPARATIONS THEREOF

[75] Inventors: Günter Neef; Ulrich Eder; Gregor Haffer; Gerhard Sauer; Rudolf Wiechert; Hermann Steinbeck, all of Berlin, Fed. Rep. of Germany

[73] Assignee: Schering, Aktiengesellschaft, Berlin and Bergkamen, Fed. Rep. of Germany

[21] Appl. No.: 150,518

[22] Filed: May 16, 1980

[30] Foreign Application Priority Data

May 17, 1979 [DE] Fed. Rep. of Germany ....... 2920184

[51] Int. Cl.³ ............................................. A61K 31/56
[52] U.S. Cl. ................................ 424/243; 260/397.45
[58] Field of Search ............................. 424/242, 243; 260/397.45

[56] References Cited

U.S. PATENT DOCUMENTS 3,781,311 12/1973 Warnant et al. ............... 260/397.45
3,810,885 5/1974 Bucourt et al. ............. 260/239.55 C

OTHER PUBLICATIONS

Comptes Rendus Academie des Sciences, (1963), 257, pp. 569–570.

Primary Examiner—Elbert L. Roberts
Attorney, Agent, or Firm—Millen & White

[57] ABSTRACT

16 α-Alkyl steroids of the formula

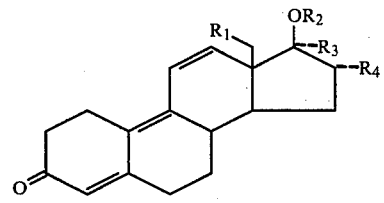

wherein
$R_1$ is hydrogen or methyl,
$R_2$ is hydrogen, alkyl, acyl, or glycosyl
$R_3$ is hydrogen or a substituted or unsubstituted, saturated or unsaturated lower hydrocarbon residue, and
$R_4$ is methyl, ethyl or propyl, exhibit strong progestational activity and a very low androgenic activity.

14 Claims, No Drawings

16 α-ALKYL STEROIDS, THEIR PREPARATION, AND PHARMACEUTICAL PREPARATIONS THEREOF

The present invention concerns 16α-alkyl steroids, a process for their preparation and pharmaceutical preparations containing them.

SUMMARY OF THE INVENTION

It is an object of this invention to provide steroids having pharmacological activity, e.g. high progestational activity with low attendant androgenic activity.

Upon further study of the specification and appended claims, further objects and advantages of this invention will become apparent to those skilled in the art.

These objects have been attained by providing 16-α-alkyl steroids of the formula

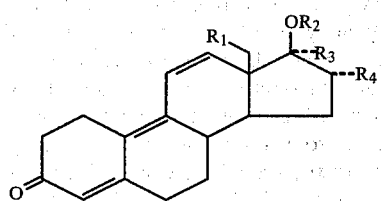

wherein
$R_1$ is hydrogen or methyl,
$R_2$ is hydrogen, alkyl, acyl or glycosyl,
$R_3$ is hydrogen or a substituted or unsubstituted saturated or unsaturated lower hydrocarbon residue, and
$R_4$ is methyl, ethyl or propyl.

DETAILED DISCUSSION

The steroids of Formula I can be unsubstituted in the 17α-position ($R_3$=H) or they can carry as the substituent $R_3$ a substituted or unsubstituted, saturated or unsaturated lower hydrocarbon residue. Such lower hydrocarbon residues include, for example, alkyl of 1–5 carbon atoms, preferably methyl and ethyl, alkenyl and alkynyl of 2–3 carbon atoms, preferably vinyl, ethynyl, and propynyl. The hydrocarbon residue can also be suitably substituted by one or several substituents such as hydroxy groups or halogen (F, Cl, Br, I) atoms, chloroethynyl being the preferred substituted hydrocarbon residue.

Alkyl groups $R_2$ can contain 1–5 carbon atoms (including $C_{3-5}$ cycloalkyl) and can optionally be interrupted by an oxygen atom (i.e. the O atom is at a non-terminal position); preferred are methyl, ethyl, methoxymethyl, methoxyethyl, ethoxyethyl and tetrahydropyranyl.

Suitable acyl groups $R_2$ are those of physiologically compatible acids i.e. such acids forming resultant steroids which are physiologically compatible. Preferred are those derived from organic carboxylic or sulfonic acids of 1–17 carbon atoms e.g. such acids which are hydrocarbons and are equivalent to the other acids included in the broad class. Such carboxylic and sulfonic acids, all of which are equivalent, can belong to the aliphatic, cycloaliphatic, aromatic, aromatic-aliphatic or heterocyclic series. These acids can moreover also be saturated or unsaturated, mono- or polybasic and/or substituted in conventional fashion for acyl groups or related steroids. Examples of suitable substituents are hydroxy, $C_{1-5}$ alkoxy, acyloxy (e.g., acyl as defined above), oxo, amino or halogen, the resultant substituted acids being equivalents of the unsubstituted acids for purpose of this invention.

Examples of such equivalent carboxylic acids include the following: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, β-cyclopentylpropionic acid, cyclohexylacetic acid, cyclohexanecarboxylic acid, phenylacetic acid, phenoxyacetic acid, mono-, di-, and trichloroacetic acid, aminoacetic acid, diethylaminoacetic acid, piperidinoacetic acid, morpholinoacetic acid, lactic acid, succinic acid, adipic acid, benzoic acid, nicotinic acid, isonicotinic acid, furan-2-carboxylic acid, β-tridecanoyloxypropionic acid, etc. Examples of suitable sulfonic acids include: methane-, ethane-, β-chloroethane-, propane-, isopropane-, butane-, cyclopentanecyclohexane-, benzene-, p-toluene-, p-chlorobenzenesulfonic acids, etc; and, furthermore, N,N-dimethyl-, N,N-diethyl-, bis(β-chloroethyl)aminosulfonic acids, etc; and pyrrolidino-, piperidino-, piperazino-, N-methylazino-, and morpholinosulfonic acids, etc.

Quite particularly preferred are alkanecarboxylic acids of 2–7 carbon atoms.

The expression "glycosyl" refers to free sugar residues, e.g., hexoses or pentoses or such sugar residues esterified with lower alkanecarboxylic acids of up to 5 carbon atoms. Examples of suitable sugars include glucose, rhamnose, ribose, and arabinose.

The 16α-alkyl steroids of formula I can be prepared by dehydrogenating a 16α-alkyl steroid of formula II

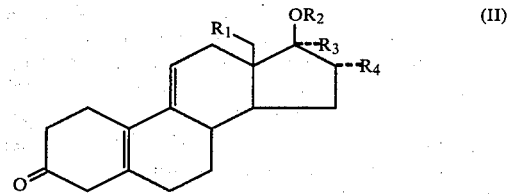

wherein $R_1$, $R_2$, $R_3$, and $R_4$ are as defined above and, optionally, subsequently saponifying an esterified secondary 17β-hydroxy group, and/or esterifying a free secondary or tertiary 17β-hydroxy group or converting it into a glycoside, or etherifying it.

The dehydrogenation of a compound of formula II can be conducted, in fully conventional manner with dehydrogenating agents. Suitable dehydrogenating agents include for example, selenium dioxide or substituted p-quinones, especially substituted p-benzoquinones, e.g. 2,3-dichloro-5,6-dicyanobenzoquinone (DDQ), 2,3-dibromo-5,6-dicyanobenzoquinone, 2,3-dicyano-4-chlorobenzoquinone, 2,3-dicyanobenzoquinone, and 2,3,5,6-tetrachlorobenzoquinone (chloranil).

The dehydrogenation is suitably conducted in an organic solvent, e.g. with substituted quinones in methylene chloride, dichloroethane, benzene, toluene, dioxane, ethyl acetate, and also in chlorobenzene, diethyl ether, ethylene glycol, dimethylformamide, nitrobenzene, dimethyl sulfoxide, etc. The reaction can take place at room temperature or at elevated temperature; preferably the reaction is conducted at room temperature under an inert gas. The dehydrogenation of Δ5(10),9(11)-steroids has been described in detail in U.S. Pat. No. 3,453,267.

The dehydrogenation with selenium dioxide takes place, for example, in dioxane under boiling conditions.

The saponification of 17β-acyloxy groups can be accomplished conventionally. For example, the saponification can be carried out with bases in an aqueous-alcoholic solution, such as with potassium carbonate in an aqueous-methanolic solution.

For the optionally following esterification of the secondary or tertiary hydroxy groups, methods which are customarily employed in steroid chemistry for esterification can be used. For example, worth mentioning is the reaction with acids or acid anhydrides in the presence of strong acids, e.g. trifluoroacetic acid or p-toluenesulfonic acid at room temperature or somewhat elevated temperature, or the reaction with an acid anhydride in the presence of a tertiary amine with heating at about 20°–200° C.

If pyridine and 4-(dimethylamino) pyridine are utilized together as tertiary amines, the esterification can be effected at room temperature.

Alkylating compounds, e.g. alkyl halogenides can be used to effect the etherifications. There also takes place in conventional fashion in the presence of a strong base, such as sodium hydroxide solution, with the use of a polar solvent, e.g. hexamethylphosphoric triamide, at 0°–50° C. or in the presence of a strong base, such as sodium hydride, with the use of an ether, such as tetrahydrofuran, at 30°–100° C.

To produce alkyl ethers, the carbon chain of which is interrupted by an oxygen atom and optionally closed to a ring, the 17-hydroxy compounds are converted into the corresponding tetrahydropyranyl or alkoxyethyl ethers with dihydropyran or alkylvinyl ethers in the presence of a strong acid, e.g. p-toluene-sulfonic acid or phosphorus oxychloride. The reaction is preferably conducted in the presence of inert solvents, such as chloroform, methylene chloride, tetrahydrofuran, dioxane, etc., at a reaction temperature of −20° to 100° C. To produce methoxymethyl ethers the 17-hydroxy compound is reacted, for example, with formaldehyde dimethylacetal in anhydrous methylene chloride in the presence of phosphorus pentoxide at room temperature.

For purposes of glycosidation, the 17-hydroxy compounds can be reacted with the appropriate 1-halogen sugars. The reaction occurs in the presence of a heavy metal salt or a heavy metal oxide, preferably in an inert organic solvent, e.g. benzene, and preferably at the boiling temperature of the solvent. Preferred heavy metal compounds are the oxides, cyanides, carbonates, or perchlorates of silver or mercury.

The compounds of formula II used as the starting materials can be prepared according to conventional methods. For example, to produce compounds of Formula II with $R_1$ being hydrogen, estrone methyl ether is first converted, according to DOS [German Unexamined Laid-Open Application] No. 2,757,157, into the corresponding 16α-alkyl estrone methyl ethers. Then analogously to the process described in U.S. Pat. No. 3,453,267, conversion is effected to the 17β-acetoxy-16α-alkyl-5(10),9(11)-estradien-3-one by reduction of the 17-ketone with sodium borohydride, Birch reduction of the aromatic methyl ether, acid hydrolysis of the Birch product to the Δ5(10)-3-oxo derivative, reaction with pyridine hydrobromide perbromide in the presence of pyridine to the Δ4,9(10)-3-oxo derivative, acetylation of the 17-hydroxy group, ketalization to the Δ5(10),9(11)-3-ketal, and subsequent acidic ketal cleavage in the presence of pyruvic acid or oxalic acid.

Other starting materials can be produced in accordance with, or analogous to methods described in U.S. Pat. No. 3,453,267.

See also the Examples herein.

The compounds of formula I possess valuable pharmacological properties. Thus, even the compounds without a substituent in the 17α-position ($R_3=H$) display a progestational activity corresponding to that of levonorgestrel and only a very low androgenic effect. The properties of the novel 16α-alkyl steroids of Formula I could not be foreseen, since the corresponding compounds without a 16α-alkyl substituent show a very strong androgenic activity (Comptes Rendus Acad. Sci. 257: 569–570 [1963]).

On the basis of their favorable pharmacological properties, the compounds of this invention can be used with particular advantage in otherwise conventional contraceptive preparations wherein they are utilized as the progestational component in combination with an estrogenically effective hormone component, e.g. ethynylestradiol, or as the sole active component, e.g., in a manner analogous to the use of the conventional progestational agent norgestrel (U.S. Pat. No. 3,959,322) or lynestrenol (U.S. Pat. No. 2,966,503).

The compounds can also be employed, however, in preparations for the treatment of gynecological disturbances such as cycle irregularities in case of inadequate function of the corpus luteum, climacteric complaints, depressive mood, etc. e.g., in a manner analogous to the known agent Cyclo-Progynova ®.

For purposes of administration to mammals, including humans, the novel compounds are processed with the additives, vehicles, and flavor-ameliorating agents customary in galenic pharmacy to form the customary forms of medicine in accordance with fully conventional methods. Especially suitable for oral application are tablets, dragees, capsules, pills, suspensions, or solutions. For parenteral application, especially suitable are oily solutions, e.g. sesame oil or castor oil solutions, which can optionally additionally contain a diluent, such as, for example, benzyl benzoate or benzyl alcohol. The concentration of the active ingredient is dependent on the form of application. Thus, tablets for oral administration contain, for example, preferably 0.01–0.5 mg of active agent, and solutions for parenteral administration contain preferably 1–100 mg of active agent per 1 ml of solution.

The dosage of the pharmaceutical preparations of this invention as usual can vary with the form and the purpose of administration. For example, the daily contraceptive dose in case of oral application is 0.05–0.5 mg of active agent of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

17β-Acetoxy-16α-methyl-5(10),9(11)-estradien-3-one (a) A solution of 5 g of 3-methoxy-1,3,5(10)-estratrien-17-one in 100 ml of ethanol, 15 ml of dimethylhydrazine and 3 ml of triethyl orthoformate is heated under reflux for 30 hours. After cooling the mixture is poured into about 500 ml of water, extracted with ethyl acetate, the ethyl acetate extracts are washed with saturated sodium chloride solution, dried over sodium sulfate, and concentrated under vacuum. The oily residue is crystallized from acetonitrile, thus obtaining 5.6 g of 3-methoxy-1,3,5(10)-estratrien-17-one N,N-dimethylhydrazone, m.p. 85°–86° C.

(b) A solution of 5 g of 3-methoxy-1,3,5(10)-estratrien-17-one N,N-dimethylhydrazone in 50 ml of absolute tetrahydrofuran (THF) is combined dropwise at 0° C. with 13 ml of a 15% solution of n-butyllithium in hexane. After this addition the mixture is stirred for 60 minutes under argon at 0° C., then 1.3 ml of methyl iodide is added dropwise thereto at 0° C., and the mixture is stirred for another 30 minutes at room temperature. To work up the mixture, it is poured into saturated ammonium chloride solution and extracted with ethyl acetate. Crystallization from acetonitrile yields 5 g of 3-methoxy-16α-methyl-1,3,5(10)-estratrien-17-one N,N-dimethylhydrazone, m.p. 122°–124° C.

(c) A solution of 1.4 g of 3-methoxy-16α-methyl-1,3,5(10)-estratrien-17-one N,N-dimethylhydrazone in 60 ml of tetrahydrofuran (THF) and 12 ml of water is combined with a solution of 1.45 g of copper(II) chloride (CuCl$_2$.2H$_2$O) in 19 ml of water and stirred at room temperature for 16 hours. The mixture is then poured into water and extracted with ethyl acetate. Crystallization from methanol yields 1.2 g of 3-methoxy-16α-methyl-1,3,5(10)-estratrien-17-one, m.p. 115°–116° C.

(d) 16.0 g of 3-methoxy-16α-methyl-1,3,5(10)-estratrien-17-one is dissolved in 200 ml of ethanol and, under ice cooling, combined dropwise with a solution of 2.1 g of sodium borohydride in 100 ml of 80% aqueous ethanol. The mixture is stirred for 16 hours at room temperature, then 1 N hydrochloric acid is gently added to the reaction solution, the latter is poured into water and extracted with ethyl acetate. Crystallization from acetonitrile yields 13.4 g of 3-methoxy-16α-methyl-1,3,5(10)-estratrien-17β-ol, m.p. 100°–102° C.

(e) A solution of 10.0 g of 3-methoxy-16α-methyl-1,3,5(10)-estratrien-17β-ol in 200 ml of absolute THF and 20 ml of tert.-butanol is dropped at −50° C. to about 500 ml of ammonia and then combined in incremental portions with 6.3 g of lithium. The mixture is agitated for 3 hours at −40° C., ammonia is allowed to evaporate overnight, the residue is taken up in about 1 liter of water, and extracted with ethyl acetate, thus obtaining 9.6 g of 3-methoxy-16α-methyl-2,5(10)-estradien-17β-ol as an amorphous crude product which is used in the subsequent stage without further purification.

9.6 g of the above product is stirred for 60 minutes at 40° C. in 400 ml of acetone and 100 ml of water with 7.5 g of oxalic acid. After cooling the mixture is poured into water, extracted with methylene chloride, the methylene chloride extracts are washed with saturated NaHCO$_3$ solution and saturated NaCl solution, dried over sodium sulfate, and concentrated, thus producing 8.5 g of 17β-hydroxy-16α-methyl-5(10)-estren-3-one which is used in the subsequent reaction without further purification.

A solution of 8.5 g of the above crude product in 390 ml of pyridine is combined under ice water cooling in incremental portions with 12.1 g of pyridine hydrobromide perbromide and stirred for 2 hours at 50° C. under argon. After cooling the mixture is poured into about 2.1 of 2 N hydrochloric acid and extracted with ethyl acetate. The ethyl acetate extracts are washed in succession with 4 N hydrochloric acid and water, dried over sodium sulfate, and concentrated. The oily crude product is chromatographed on silica gel with petroleum ether/ethyl acetate, yielding 7.8 g of 17β-hydroxy-16α-methyl-4,9(10)-estradien-3-one, m.p. 146°–148° C. (from ethyl acetate/diisopropyl ether).

(f) A solution of 7.8 g of 17β-hydroxy-16α-methyl-4,9(10)-estradien-3-one in 25 ml of pyridine and 8 ml of acetic anhydride is stirred for 6 hours at 50° C. under argon. After cooling the mixture is poured into saturated NaHCO$_3$ solution and extracted with ethyl acetate. The ethyl acetate extracts are washed in succession with water, 2 N hydrochloric acid, and saturated NaCl solution, dried over sodium sulfate, and concentrated. Crystallization from ether yields 6.6 g of 17β-acetoxy-16α-methyl-4,9(10)-estradien-3-one, m.p. 124°–126° C.

(g) A solution of 3.6 g of 17β-acetoxy-16α-methyl-4,9(10)-estradien-3-one in 6.5 ml of ethanol, 30 ml of triethyl orthoformate, and 100 mg of p-toluenesulfonic acid is stirred at room temperature for 45 minutes. Then the mixture is poured into saturated NaHCO$_3$ solution and extracted with ethyl acetate. After concentration 3.8 g of 17β-acetoxy-16α-methyl-5(10),9(11)-estradiene 3,3-diethylketal is produced as a colorless oil which is used in the following stage without purification.

A solution of 3.8 g of the above crude product in 150 ml of acetone and 20 ml of water is stirred, after the addition of 3.0 g of oxalic acid, for 60 minutes at 40° C. Then the mixture is poured into saturated NaHCO$_3$ solution and extracted with ethyl acetate, thus obtaining 3.2 g of 17β-acetoxy-16α-methyl-5(10),9(11)-estradien-3-one as a colorless oil.

EXAMPLE 2

17β-Acetoxy-16α-ethyl-5(10),9(11)-estradien-3-one

According to 1(b), 20.2 g of 16α-ethyl-3-methoxy-1,3,5(10)-estratrien-17-one, N,N-dimethylhydrazone, m.p. 101°–103° C. (from acetonitrile) is obtained from 20.4 g of 3-methoxy-1,3,5(10)-estratrien-17-one N,N-dimethylhydrazone after metallization and alkylation with 9.2 ml of bromoethane. By reaction with CuCl$_2$.2H$_2$O according to 1(c), the 17-ketone is obtained from the hydroazone and then, by reduction of the 17-ketone with sodium borohydride according to 1(d), 16.0 g of 16α-ethyl-3-methoxy-1,3,5(10)-estratrien-17β-ol, m.p. 75°–76° C. (from methanol) is prepared. 10.0 g of 16α-ethyl-3-methoxy-1,3,5(10)-estratrien-17β-ol is subjected analogously to 1(e) in succession to Birch reduction, acid hydrolysis, and reaction with pyridine hydrobromide perbromide, thus obtaining 7.8 g of 16α-ethyl-17β-hydroxy-4,9(10)-estradien-3-one, m.p. 132°–135° C. (from ethyl acetate/diisopropyl ether). This product is converted analogously to 1(f) with acetic anhydride/pyridine into the 17-acetate, m.p. 124°–126° C. (from ether) and analogously to 1(g) by ketalization and subsequent ketal cleavage into the 17β-acetoxy-16α-ethyl-5(10),9(11)-estradien-3-one.

EXAMPLE 3

17β-Acetoxy-16α-propyl-5(10),9(11)-estradien-3-one

According to 1(b) 5.4 g of 3-methoxy-16α-propyl-1,3,5(10)-estratrien17-one N,N-dimethylhydrazone, m.p. 83°–85° C., is obtained from 5.0 g of 3-methoxy-1,3,5(10)-estratrien-17-one N,N-dimethylhydrazone with 1-bromopropane after crystallization from acetonitrile. By reaction with $CuCl_2.2H_2O$ according to 1(c) 4.1 g of 3-methoxy-16α-propyl-1,3,5(10)-estratrien-17-one, m.p. 98°–100° C. (from acetonitrile), is obtained from 5.0 g of hydrazone, and 3.2 g of the 17-ketone yields with sodium borohydride according to 1(d) 2.1 g of 3-methoxy-16α-propyl-1,3,5(10)-estratrien-17β-ol, m.p. 54°–56° C. (from acetonitrile). By Birch reduction, acid hydrolysis, reaction with pyridine hydrobromide perbromide, acetylation in the 17-position, ketalization and deketalization in the 3-position 17β-acetoxy-16α-propyl-5(10),9(11)-estradien-3-one is obtained as an oil.

To prepare compounds of general Formula II with $R_1$ meaning methyl, 18-methylestrone methyl ether is converted with bis(dimethylamino)tert.-butoxymethane into the 16-dimethylaminomethylene compound; reaction of the latter with alkyl lithium or alkyl magnesium bromide leads to the 16-alkylidene compound which is converted by hydrogenation to the 16β-alkyl compound and by acidic or alkaline isomerization to the 16β-alkyl-18-methylestrone methyl ether. The further reactions take place in the same way as in case of the compounds with $R_1$=hydrogen.

EXAMPLE 4

17β-Acetoxy-16α-ethyl-18-methyl-5(10),9(11)-estradien-3-one (a) A mixture of 10 g of 3-methoxy-18-methyl-1,3,5(10)-estratrien-17-one and 15 g of bis(dimethylamino)tert.-butoxymethane is stirred for 3 hours at 160° C. After cooling the mixture is combined with 50 ml of ethanol and left at −5° C. for crystallizing purposes. After filtering off and drying, 10.6 g of 16-dimethylaminomethylene-3-methoxy-18-methyl-1,3,5(10)-estratrien-17-one is obtained, m.p. 157°–159° C.

(b) A solution of 5.0 g of 16-dimethylaminomethylene-3-methoxy-18-methyl-1,3,5-(10)-estratrien-17-one in 150 ml of toluene is combined at −10° C. dropwise with 30 ml of a 5% solution of methyllithium in ether. After this dropwise addition the mixture is stirred for 15 minutes at −10° C., then about 10 ml of water is added to the reaction solution and the latter then poured into about 200 ml of 0.5 N hydrochloric acid. The organic phase is separated, dried over sodium sulfate, and concentrated. After crystallization of the residue from methanol 4.9 g of 16-ethylidene-3-methoxy-18-methyl-1,3,5(10)-estratrien-17-one is obtained, m.p. 155°–157° C.

(c) A solution of 1.3 g of 16-ethylidene-3-methoxy-18-methyl-1,3,5(10)-estratrien-17-one in 180 ml of ethanol is hydrogenated, after adding 130 mg of 10% palladium charcoal, at room temperature and normal pressure. After absorbing 115 ml of hydrogen the reaction product is filtered off from the catalyst and the filtrate concentrated. Crystallization from methanol yields 1.3 g of 16β-ethyl-3-methoxy-18-methyl-1,3,5(10)-estratrien-17-one, m.p. 101°–102° C.

(d) A solution of 1.3 g of 16β-ethyl-3-methoxy-18-methyl-1,3,5(10)-estratrien-17-one in 14.5 ml of glacial acetic acid and 2 ml of concentrated hydrochloric acid is stirred for 16 hours at room temperature. Then the mixture is poured into water, extracted with ethyl acetate, the ethyl acetate extracts washed in succession with saturated $NaHCO_3$ solution and saturated NaCl solution, dried over sodium sulfate, and concentrated under vacuum. The oily crude product is reduced according to 1(d) with sodium borohydride. Chromatography on silica gel with petroleum ether/ethyl acetate yields 620 mg of 16α-ethyl-3-methoxy-18-methyl-1,3,5(10)-estratrien-17β-ol, m.p. 112°–114° C. (from methanol).

By Birch reduction, acid hydrolysis, reaction with pyridine hydrobromide perbromide, acetylation in 17-position, ketalization, and deketalization in the 3-position, 17β-acetoxy-16α-ethyl-18-methyl-5(10),9(11)-estradien-3-one is obtained as an oil.

EXAMPLE 5

17α-Ethynyl-17β-hydroxy-16α-methyl-5(10),9(11)-estradien-3-one (a) A solution of 4.58 g of 17β-hydroxy-16α-methyl-4,9(10)-estradien-3-one (prepared according to 1[e]) in 200 ml of acetone is combined under ice water cooling dropwise with 8.5 ml of Jones reagent (J. Chem. Soc. [London] 1946, 39). The mixture is stirred, after this addition, at room temperature for 20 minutes, thereafter poured into water, and extracted with methylene chloride. The methylene chloride extracts are washed with saturated sodium chloride solution, dried over sodium sulfate, and concentrated. Crystallization from ethyl acetate/diisopropyl ether yields 4.3 g of 16α-methyl-4,9(10)-estradiene-3,17-dione, m.p. 140°–143° C.

(b) A solution of 4.2 g of the dione obtained under (a) in 8 ml of ethanol and 38 ml of triethyl orthoformate is stirred, after adding 100 mg of p-toluenesulfonic acid, for 45 minutes at room temperature. The mixture is then poured into saturated $NaHCO_3$ solution and extracted with ethyl acetate. Yield: 4.4 g of 3,3-diethoxy-16α-methyl-5(10),9(11)-estradien-17-one as a colorless oil which is used in the subsequent stage without further purification.

(c) Under ice water cooling, an acetylene stream is conducted over a period of 30 minutes through 140 ml of absolute tetrahydrofuran (THF). Then 36 ml of a 15% solution of n-butyllithium in hexane is added dropwise at 0° C. to the reaction mixture and acetylene is again passed through the solution (10 minutes). Maintaining the temperature (0° C.), a solution of 4.1 g of the ketal obtained under (b) in 40 ml of THF is added dropwise to the reaction mixture and the latter is stirred for 60 minutes at 0° C. For working up purposes the mixture is poured into saturated $NH_4Cl$ solution and extracted with ethyl acetate.

The oily crude product is taken up in 180 ml of acetone and 40 ml of water and, after adding 3.4 g of oxalic acid, agitated for 60 minutes at 40° C. Then the mixture is poured into water and extracted with ethyl acetate. Chromatography on silica gel with petroleum ether/acetone yields 2.6 g of 17α-ethynyl-17β-hydroxy-16α-methyl-5(10),9(11)-estradien-3-one, m.p. 165°–168° C. (ethyl acetate/ether).

Analogously, the corresponding 17α-ethynyl-16α-ethyl-17β-hydroxy-5(10),9(11)-estradien-3-one is obtained from 16α-ethyl-17β-hydroxy-4,9(10)-estradien-3-one (prepared according to 2).

Instead of using an organometallic ethynyl compound, the 17-ketone can also be reacted with other organometallic hydrocarbon compounds (organometallic R$_3$-compounds). Examples for suitable organometallic R$_3$-compounds are alkyl, alkenyl, and alkynyl magnesium halides, especially methyl-, ethyl-, vinyl-, ethynyl-, and propynylmagnesium bromide or iodide.

For purposes of chloroethynylation, the organometallic chloroethynyl compound can be formed in situ from 1,2-dichloroethylene and an ethereal alkyllithium solution, e.g. methyl- or butyllithium solution. Suitable solvents are tetrahydrofuran and diethyl ether.

As described for the process products of general Formula I, the starting compounds of general Formula II can also be modified, by saponification of the 17β-acetoxy group and optional reesterification, forming of the glycoside, or etherification of the free secondary or tertiary 17β-hydroxy group, in the 17-position.

EXAMPLE A 3.2 g of 17β-acetoxy-16α-ethyl-5(10),9(11)-estradien-3-one is dissolved in 120 ml of toluene and 40 ml of methylene chloride and combined at room temperature dropwise with a solution of 5.5 g of dichlorodicyano-p-benzoquinone in 80 ml of toluene and 20 ml of methylene chloride. The mixture is stirred for 16 hours at room temperature, filtered over neutral aluminum oxide, and concentrated. After crystallization from diethyl ether, 2.8 g of 17β-acetoxy-16α-ethyl-4,9,11-estratrien-3-one is obtained, m.p. 95°–98° C.

EXAMPLE B

Analogously to Example A, 3.0 g of 17β-acetoxy-16α-methyl-4,9,11-estratrien-3-one, m.p. 120°–123° C. (from diethyl ether) is obtained from 3.6 g of 17β-acetoxy-16α-methyl-5(10),9(11)-estradien-3-one.

EXAMPLE C

A solution of 2.5 g of 17β-acetoxy-16α-ethyl-4,9,11-estratrien-3-one in 120 ml of methanol and 5 ml of water is stirred, after adding 6.0 g of potassium carbonate, for 4 hours at room temperature. The mixture is then poured into water and extracted with ethyl acetate. Crystallization of the crude product from ethyl acetate yields 1.9 g of 16α-ethyl-17β-hydroxy-4,9,11-estratrien-3-one, m.p. 139°–141° C.

EXAMPLE D

Analogously to Example C 2.5 g of 17β-acetoxy-16α-methyl-4,9,11-estratrien-3-one is saponified. Crystallization from acetonitrile yields 1.95 g of 17β-hydroxy-16α-methyl-4,9,11-estratrien-3-one, m.p. 149°–151° C.

EXAMPLE E 1.9 g of 17α-ethynyl-17β-hydroxy-16α-methyl-5(10),9(11)-estradien-3-one is dissolved in 60 ml of benzene and 20 ml of methylene chloride and combined at room temperature dropwise with a solution of 3.5 g of dichlorodicyano-p-benzoquinone. The mixture is agitated for 5 hours at room temperature and worked up as described in Example A. Crystallization of ether yields 1.65 g of 17α-ethynyl-17β-hydroxy-16α-methyl-4,9,11-estratrien-3-one, m.p. 176°–179° C.

EXAMPLE F

Analogously to Example E, 3.4 g of 17α-ethynyl-16α-ethyl-17β-hydroxy-4,9,11-estratrien-3-one, m.p. 164°–166° C. (methylene chloride/diisopropyl ether) is obtained from 3.6 g of 17α-ethynyl-16α-ethyl-17β-hydroxy-5(10),9(11)-estradien-3-one.

EXAMPLE G

Analogously to Example A, 3.1 g of 17β-acetoxy-16α-ethyl-18-methyl-5(10),9(11)-estradien-3-one (prepared according to D) yields, after crystallization from ether, 2.0 g of 17β-acetoxy-16α-ethyl-18-methyl-4,9,11-estratrien-3-one, m.p. 123°–127° C.

EXAMPLE H

Analogously to Example C 1.5 g of 17β-acetoxy-16α-ethyl-18-methyl-4,9,11-estratrien-3-one is saponified. Crystallization from acetonitrile yields 1.35 g of 16α-ethyl-17β-hydroxy-18-methyl-4,9,11-estratrien-3-one, m.p. 184°–187° C.

EXAMPLE I

A solution of 2.0 g of 16α-ethyl-17β-hydroxy-4,9,11-estratrien-3-one in 30 ml. of absolute tetrahydrofuran is stirred with 3 ml of dihydropyran and 0.01 ml of phosphorus oxychloride for 3 hours at room temperature. The mixture is then poured into 5% NaHCO$_3$ solution and extracted with ether. The ether extracts are washed with saturated NaCl solution, dried over Na$_2$SO$_4$, and concentrated. A light-yellow oil remains (2.2 g) which is column-chromatographed over silica gel with petroleum ether/ethyl acetate. Crystallization of the main fraction from ether/petroleum ether yields 1.4 g of 16α-ethyl-17β-tetrahydropyran-2-yloxy-4,9,11-estratrien-3-one, m.p. 126°–129° C. (mixture of isomers).

EXAMPLE K

A solution of 1.5 g of 17β-acetoxy-16α-propyl-5(10),9(11)-estradien-3-one in 100 ml of methylene chloride is dehydrogenated with 1.8 g of dichlorodicyano-p-benzoquinone under the conditions of Example 1. After crystallization from diisopropyl ether, 1.4 g of 17β-acetoxy-16α-propyl-4,9,11-estratrien-3-one is obtained, m.p. 108°–109° C.

EXAMPLE L

Analogously to Example 3 1.2 g of 17β-acetoxy-16α-propyl-4,9,11-estratrien-3-one is saponified. Crystallization from diisopropyl ether yields 1.0 g of 17β-hydroxy-16α-propyl-4,9,11-estratrien-3-one, m.p. 135°–136° C.

EXAMPLE M

| Tablet Composition | |
|---|---|
| 0.075 mg. | 16α-ethyl-17β-hydroxy-4,9,11-estratrien-3-one |
| 0.030 mg. | 17α-ethynylestradiol |
| 109.895 mg. | lactose (DAB 6) [German Pharmacopoeia] |
| 8.000 mg. | corn starch (USP XVI) |
| 1.000 mg. | magnesium stearate (USP XVI) |
| 1.000 mg. | talc |
| 120.000 mg. | total weight of the tablet |

EXAMPLE N

| Dragee Composition | |
|---|---|
| 0.050 mg. | 16α-ethyl-17β-hydroxy-4,9,11-estratrien-3-one |
| 0.030 mg. | 17α-ethynylestradiol |
| 31.920 mg. | lactose |
| 18.425 mg. | corn starch |
| 2.060 mg. | polyvinylpyrrolidone 25 |
| 0.010 mg. | methyl p-hydroxybenzoate [methylparaben] |
| 0.005 mg. | propyl p-hydroxybenzoate [propylparaben] |
| 2.500 mg. | talc |
| 55.000 mg. | total weight of the tablet which is made into |

| -continued |   |
|---|---|
| Dragee Composition |   |
| a dragee with a weight of about 90 mg. with the usual sugar mixture |   |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 16α-alkyl steroid of the formula

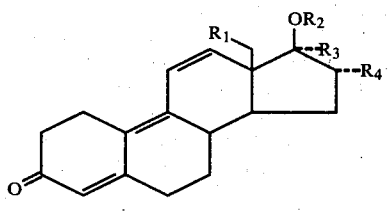

wherein

R$_1$ is hydrogen or methyl,

R$_2$ is hydrogen, C$_{1-5}$ alkyl, C$_{3-5}$ cycloalkyl, C$_{1-5}$ alkyl or C$_{3-5}$ cycloalkyl interrupted by 0 at a nonterminal position, the acyl residue of a C$_{1-17}$ hydrocarbon carboxylic or sulfonic acid, glycosyl or glycosyl esterified by a C$_{1-5}$ alkanoyl, R$_3$ is hydrogen, C$_{1-5}$ alkyl, C$_{2-3}$ alkenyl, C$_{2-3}$ alkynyl or one of the latter three substituted by OH or halo, and R$_4$ is methyl, ethyl or propyl.

2. 17β-Acetoxy-16α-ethyl-4,9,11-estratrien-3-one, a compound of claim 1.

3. 16α-Ethyl-17β-hydroxy-4,9,11-estratrien-3-one, a compound of claim 1.

4. 17β-Acetoxy-16α-methyl-4,9,11-estratrien-3-one, a compound of claim 1.

5. 17β-Hydroxy-16α-methyl-4,9,11-estratrien-3-one, a compound of claim 1.

6. 17β-Acetoxy-16α-propyl-4,9,11-estratrien-3-one, a compound of claim 1.

7. 17α-Ethynyl-17β-hydroxy-16α-methyl-4,9,11-estratrien-3-one, a compound of claim 1.

8. 17α-Ethynyl-16α-ethyl-17β-hydroxy-4,9,11-estratrien-3-one, a compound of claim 1.

9. 17β-Acetoxy-16α-ethyl-18-methyl-4,9,11-estratrien-3-one, a compound of claim 1.

10. 16α-Ethyl-17β-hydroxy-18-methyl-4,9,11-estratrien-3-one, a compound of claim 1.

11. 16α-Ethyl-17β-tetrahydropyran-2-yloxy-4,9,11-estratrien-3-one, a compound of claim 1.

12. 17β-Hydroxy-16α-propyl-4,9,11-estratrien-3-one, a compound of claim 1.

13. A pharmaceutical composition comprising a progestationally effective amount of a compound of claim 1 and a pharmaceutically acceptable carrier.

14. A method of achieving progestational effects in a patient in need of such treatment comprising administering to the patient a progestationally effective amount of a compound of claim 1.

* * * * *